United States Patent [19]

Kadota et al.

[11] Patent Number: 4,523,484
[45] Date of Patent: Jun. 18, 1985

[54] DILUTION PIPETTER

[75] Inventors: Toshimi Kadota, Uji; Jugoro Suzuki; Shigeki Matsui, both of Kyoto, all of Japan

[73] Assignee: Shimadzu Corporation, Kyoto, Japan

[21] Appl. No.: 535,671

[22] Filed: Sep. 26, 1983

[51] Int. Cl.$^3$ .......................... G01N 1/10; B01L 3/02
[52] U.S. Cl. .................. 73/864.12; 73/864.16; 73/864.22
[58] Field of Search ........... 73/864.12, 864.16, 864.22; 422/100

[56] References Cited

U.S. PATENT DOCUMENTS

| 3,800,984 | 4/1974 | Phelan | 422/100 |
| 3,869,068 | 3/1975 | Chen | 73/864.22 |
| 3,994,687 | 11/1976 | Engelbrecht | 73/864.22 |
| 4,141,469 | 2/1979 | Lee | 73/864.22 |

Primary Examiner—S. Clement Swisher
Attorney, Agent, or Firm—Hubbell, Cohen, Stiefel & Gross

[57] ABSTRACT

A dilution pipetter comprising a diluent sucking probe, a sample probe for sucking and discharging a liquid sample, a diluent discharging probe disposed adjacent to the sample probe, a plunger pump of small plunger diameter selectively communicating with the diluent sucking probe or the sample probe by a first switching means, and a plunger pump of large plunger diameter selectively communicated with the diluent sucking probe, the sample probe or the diluent discharging probe by a second switching means. The dilution pipetter is useful as, e.g., an element of a clinical chemistry analyzer which is used to conduct numbers of reactions for small quantities of a liquid sample such as serum of the warm blooded animal including humans.

8 Claims, 10 Drawing Figures

DILUTION PIPETTER

BACKGROUND OF THE INVENTION

1. Field of the Invention

This invention concerns a dilution pipetter and, more specifically, it relates to a dilution pipetter for distributing a liquid sample each by a small volume to a plurality of reaction tubes respectively for dilution. The dilution pipetter of this invention is useful as, e.g., an element of a clinical chemistry analyzer which is used to conduct a number of reactions for small quantities of a liquid sample such as serum of the warm blooded animals including humans.

2. Description of the Prior Art

A dilution pipetter 1 as shown in FIG. 1 has heretofor been used [e.g., Simadzu Review, Vol. 38 No. 2 99-111 (1981)]. In the pipetter 1, liquid sample S is sucked from a sample cup 9 into a sample probe 3 by the sucking operation of a plunger pump 6 of small diameter while turning a first switching valve 5 to a normally closed (NC) position. Upon distributing the liquid sample S, the sample probe 3 is moved to a reaction tube 10 and then a diluent D is sucked through a diluent suction probe 2 by the sucking operation of the plunger pump 6 while turning the first switching valve 5 to a normally opened (NO) position. Then, the diluent D is sent to the sample probe 3 by the discharging operation of the plunger pump 6 to thereby push out the sample S in the sample probe 3 while turning the first switching valve 5 to the NC position. The diluent D is supplied through a diluent discharge probe 4 by the sucking operation of a plunger pump 8 of large diameter while turning a second switching valve 7 to the NC position and by the subsequent discharging operation of the plunger pump 8 while turning the second switching valve 7 to the NC position. Usually, the diluent discharge probe 4 is disposed in adjacent with the sample probe 3 so that the diluent liquid D discharged from the probe 4 flows to the probe 3 in order not to leave a droplette of the sample S at the top end of the sample probe 3.

In a case of distributing the sample S over a plurality of reaction tubes 10, 10', . . . , a large amount of the sample S has to be sucked at first into the sample probe 3. However, it takes a considerably long time for sucking such a large amount of liquid in the conventional pipetter since the plunger diameter of the pump 6 is small and thus needs a longer plunger stroke. Although the sucking time may be shortened by enlarging the plunger diameter to decrease the plunger stroke, this will lead to the reduction in the accuracy for the distributional ejection of the sample.

SUMMARY OF THE INVENTION

Accordingly, it is the object of this invention to overcome the foregoing problem in the sucking time, that is, to shorten the sucking time without reducing the accuracy in the distributional ejection of a liquid sample.

This invention provides a dilution pipetter comprising a diluent sucking probe, a sample probe for sucking and discharging a liquid sample, a diluent discharging probe disposed in adjacent to the sample probe, a plunger pump of small plunger diameter selectively communicating with the diluent sucking probe or the sample probe by a first switching means, and a plunger pump of large plunger diameter selectively communicating with the diluent sucking probe, the sample probe or the diluent discharging probe by a second switching means.

Although there is no particular restriction of the specific values for large and small diameters of plungers, the large plunger pump generally has a plunger diameter at least greater by the factor of $\sqrt{2}$ than the plunger diameter for the small plunger pump.

DESCRIPTION OF THE PREFERRED EMBODIMENT

Figure 1:
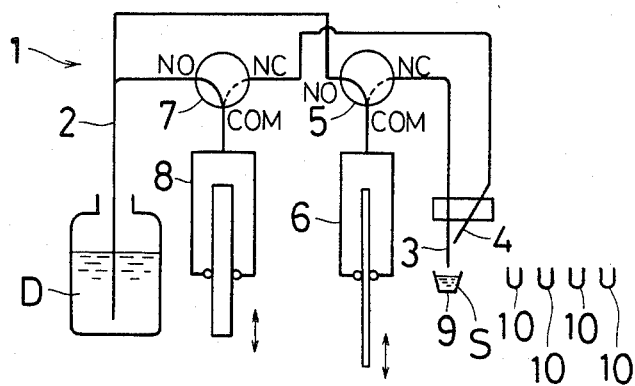
FIG. 1 is a schematic structural view illustrating one embodiment of a conventional prior art dilution pipetter.
Figure 2:
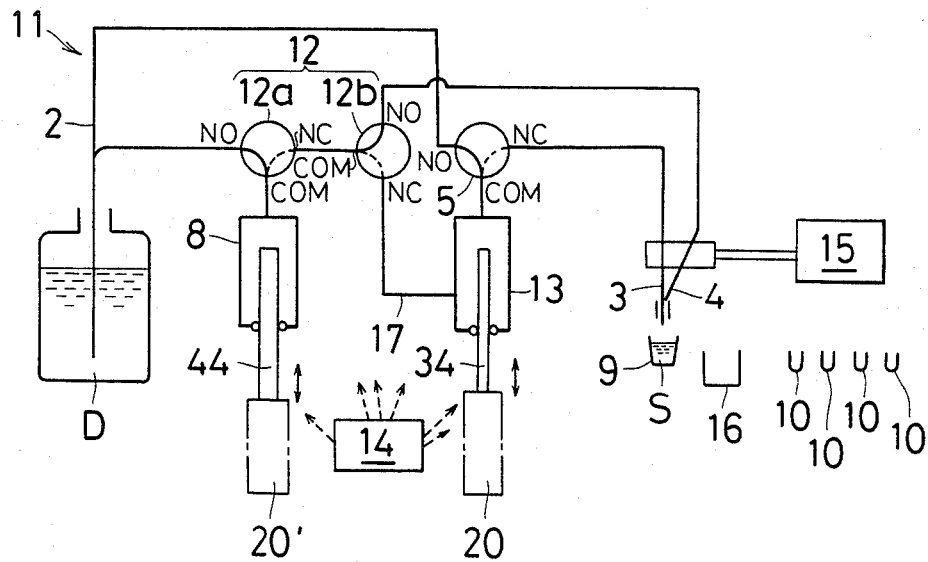
FIG. 2 is a schematic structural view illustrating a preferred embodiment of a dilution pipetter according to this invention.

FIG. 2 shows a dilution pipetter 11 as a preferred embodiment according to this invention, in which a diluent sucking probe 2, a sample probe 3, a diluent discharging probe 4, a first switching valve 5 and a plunger pump 8 of large diameter respectively have the same constitutions as those of the conventional pipetter 1 shown in FIG. 1 and carry the same reference numerals as in FIG. 1.

A second switching valve 12, different from the prior art one, comprises two 3-way switching valves 12a, 12b. In short, the two valves function so as to selectively communicate the plunger pump 8 of large diameter with the diluent sucking probe 2, the diluent discharging probe 4 or the sample probe 3 by way of a plunger pump 13 of small diameter.

The dilution pipetter 11 in this embodiment is specifically designed for use with a biochemical analyzer, in which the plunger diameter of the pump 8 of large diameter is set, for example, to 4 mm–6 mm and the plunger diameter of the pump 13 of small diameter is set, for example, to 1 mm–2 mm in most cases.

Referring to one specific embodiment for the explanation, the plunger diameter of the pump 8 is 5.05 mm and that for the plunger pump 13 is 1.60 mm.

The plunger pump 13 of small diameter is connected to the first switching valve 5, as well as by way of the second switching valve 12 to the plunger pump 8 of large diameter.

The plunger for each of the plunger pumps 8 and 13 may be driven by transmitting the rotation of a pulse motor to a screw shaft and converting the rotational movement of the screw shaft by way of an engaging nut into a linear movement of a moving member, which is interlocked with the plunger. However, since a driving mechanism 20 shown in FIGS. 3–6 results in little backrush, it can provide an exact displacement of the plunger and, accordingly, improve the accuracy of the ejection of the dilution pipetter 11.

The driving mechanism 20 shown in FIGS. 3–6 will now be explained for the drive of the plunger pump 13 of small diameter, although the plunger pump 8 of large diameter can be driven quite in the same manner.

The plunger driving mechanism 20 shown in FIGS. 3–6 comprises a cylinder 24 secured to a rotational shaft 23 of a pulse motor 22, a belt 26 secured at a portion thereof with a screw 25 to the surface of the cylinder 24 and wound therearound so as not to overlap, a moving member 33 slidably held between opposing guide grooves 31, 32 in guide members 29, 30, to which the both ends of the belt 26 are secured with screws 27, 28, and a plunger 34 mounted at one end of the moving member 33 along the advancing direction thereof and reciprocating while being sealed within the plunger pump 13 of small diameter.

Figure 3:
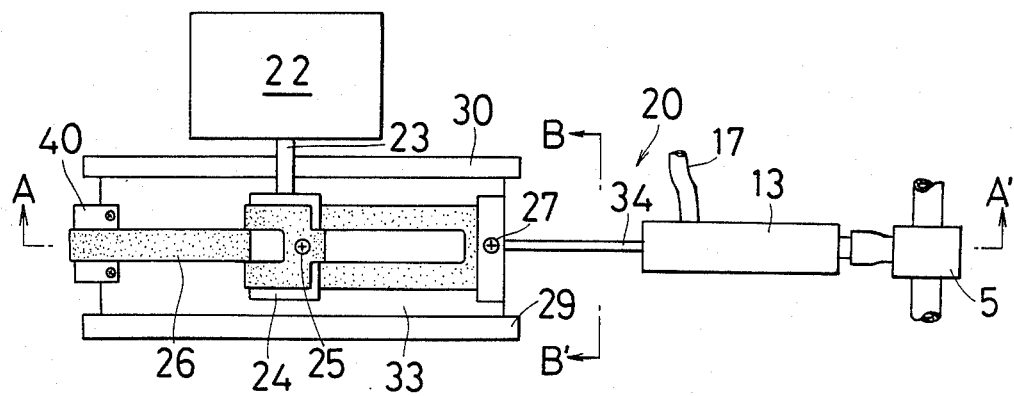
FIG. 3 is a front elevational view showing one embodiment of a plunger driving mechanism.
Figure 4:
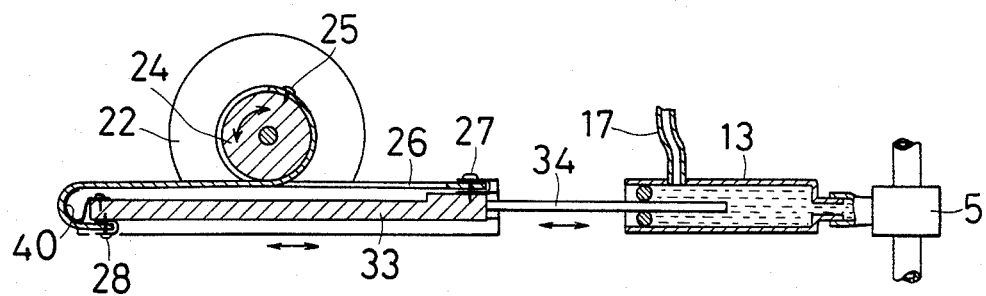
FIG. 4 is a cross sectional view taken along lines A - A' in FIG. 3.
Figure 5:
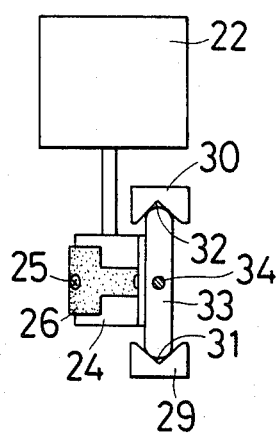
FIG. 5 is a cross sectional view taken along lines B - B' in FIG. 3.
Figure 6:
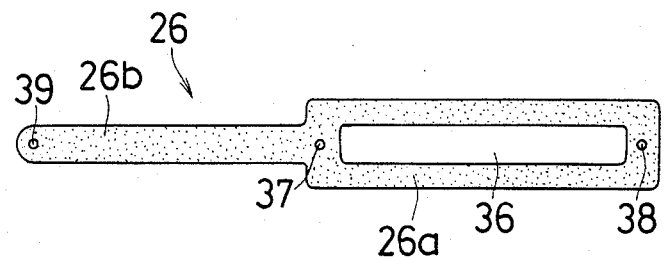
FIG. 6 is a front elevational view for a belt.

The belt 26 is usually made of a stainless steel sheet of about 50–100 μm in thickness and it comprises a broad wide portion 26a having an elongated hole 36 and a narrow wide portion 26b being capable of being accommodated in the elongated hole 36, for example, as shown in FIG. 6, so that the belt 36 can be wound around the surface of the cylinder 24 with no overlap. The belt 26 is wound around the surface of the cylinder 24 by securing it at an aperture 37 formed at the central portion thereof to the surface of the cylinder 24 with a screw 25, winding the narrow wide portion 26b while inserting the portion through the elongated hole 36 in the broad wide portion 26a so as to cross the both ends to each other as shown in FIG. 3, securing one end of the broad wide portion 26a at the aperture 38 at one end thereof to the upper surface on one end of the moving member 33 with the screw 27 and securing the other end of the small wide portion 6b at the aperture 39 formed therein to the rear side at the other end of the moving member 33 with the screw 28. In order to eliminate the slip between the belt 26 and the cylinder 24 during the rotation of the pulse motor 22 for improving the accuracy of the plunger driving mechanism 20, a leaf spring 40 is attached in an arc shape around the other end of the moving member 33 and the narrow wide portion 26b of the belt 26 is turned back toward the rear side of the moving member 33 over the leaf spring 40, by which the belt 26 can be stretched desirably by the resiliency of the leaf spring 40. The position for mounting the leaf spring 40 is not restricted to the position illustrated in the drawing, and any other resilient means than the leaf spring may also be used.

Although the belt 26 is explained as being directly wound around the cylinder 24 secured to the rotational shaft 23 of the pulse motor 22 in the foregoing embodiment, it is of course possible to adjust the moving speed of the plunger 34 by disposing an adequate decelerating means such as a timing belt between the pulse motor 22 and the cylinder 24. In addition, if the increase in the working life of the belt 26 is intended for economizing the maintenance cost, it is desired that: (a) the ratio of the thickness of the belt 26 to the diameter for the cylinder 24 is made as small as posssible, (b) the load exerted on the belt 26 is decreased or (c) photoetching is applied to the profiling line for the belt 26 or to the punching line for the elongate hole 36 so as to render them as smooth as possible.

In the plunger driving mechanism 20 as described above, in which the moving member 33 is linearly moved reciprocally by way of the belt 26 wound around the cylinder 24 from the rotation of the pulse motor 22, since the force of the belt 26 exerting on the moving member 33 is aligned with the moving direction of the member 33, the torque transmission efficiency can be improved as compared with the usual case and the pulse motor 22 required for the actuation of the plunger pump can be reduced in size. Further, the accuracy for the drive of the plunger can be improved.

Figure 7:
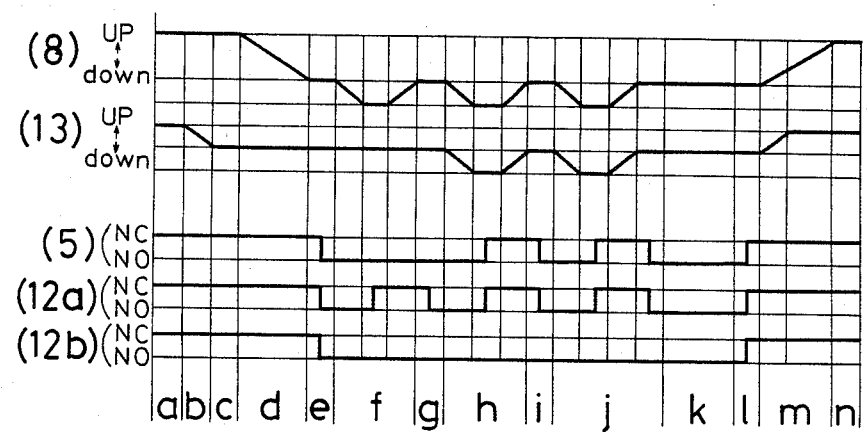
FIG. 7 is a time chart showing one example of the operation of the dilution pipetter shown in FIG. 2.

The operation of the dilution pipetter 11 according to this embodiment will be explained referring to FIG. 7 in the order of the sequential time points represented by the symbols (a)–(n) indicated at the lowermost part of the chart. The operation is carried out by the control circuit 14.

(a) The dilution pipetter 11 is in a stand-by position. The sample probe 3 and the diluent discharging probe 4 are maintained by a known moving mechanism 15 at positions where their top ends are exposed to air. All of the flowing channels are filled with the diluent D.

(b) Air is slightly sucked to the top end of the sample probe 3 by the plunger pump 13 of small diameter, which is necessary for avoiding the mixing of the diluent D previously filled in the sample probe 3 and the sample S to be sucked subsequently.

(c) The sample probe 3 is immersed by the moving mechanism 15 into the sample S.

(d) The sample S is sucked into the sample probe 3 by the plunger pump 8 of large diameter. In a specific example, the plunger 44 for the plunger pump 8 of large diameter is drawn by 20 mm and 400 μl of the sample S is sucked.

(e) The sample probe 3 and the diluent discharging probe 4 are moved by the moving mechanism 15 to a known probe cleaning cup 16.

(f) The plunger pump 8 of large diameter sucks the diluent D through the diluent sucking probe 2 and then discharges the same through the diluent discharging probe 4, by which the sample S deposited to the outside of the sample probe 3 is washed out.

(g) The sample probe 3 and the diluent discharging probe are moved by the moving mechanism 15 to a first reaction tube 10.

(h) The plunger pump 13 of small diameter sucks the diluent D by a predetermined amount from the diluent sucking probe 2 and then transfers the same to the sample probe 3, by which the sample S having been sucked in the sample probe 3 is discharged by the predetermined amount to the first reaction tube 10. In a specific example, the plunger 34 for the plunger pump 13 of small diameter is reciprocated by 7.5 mm stroke, in which the diluent D is sucked and the sample S is discharged, each by 15 μl. While on the other hand, the plunger pump 8 of large diameter sucks the diluent D from the diluent sucking probe 2 and then discharges the same from the diluent discharging probe 4 to supply the diluent D into the first reaction tube 10. In a specific example, the plunger 44 reciprocates by 2.5 mm stroke to thereby discharge the diluent D by 50 μl.

(i) The sample probe 3 and the diluent discharging probe 4 are moved by the moving mechanism 15 to a second reaction tube 10.

(j) The same procedures as in the step (h) are repeated for a second reaction tube 10.

(k) The same procedures as in the steps (i) and (j) are repeated for other reaction tubes 10, 10', . . . In a specific example, the sample is distributed, for instance, over 20 reaction tubes.

(l) The sample probe 3 and the diluent discharging probe 4 are moved by the moving mechanism 15 to the probe cleaning cup 16.

(m) The diluent D is discharged from the sample probe 3 by the plunger pump 8 and the plunger pump 13 to wash out the inside of the sample probe 3.

(n) The sample probe 3 and the diluent discharging probe 4 are returned to their stand-by positions by the moving mechanism 15.

As described above, according to the dilution pipetter 11, since the sample S is sucked by the plunger pump 8 of large diameter, the problem of taking a long sucking time can be dissolved. Assuming that the moving speed is identical between the plungers 33 and 34, the sucking time can be shortened by about 1/7 to that of the prior pipetter. While on the other hand, since the distributional ejection of the liquid sample S is carried out from the plunger pump 13 of small diameter, the accuracy for the distributional ejection is not reduced.

In another embodiment, the second switching valve 12 may be replaced with a 4-way switching valve.

In a further embodiment, the channel 17 shown in FIG. 2, instead of connected to an optional position of a channel from the plunger pump 13 of small diameter to the sample probe 3, because it is only required that the plunger pump 8 of large diameter and the sample probe 3 can eventually be communicated by way of the second switching valve 12. However, the connection as shown in the dilution pipetter 11 illustrated above is most preferred in order to desirably discharge air which may accidentally be included into the channel.

Figure 8:
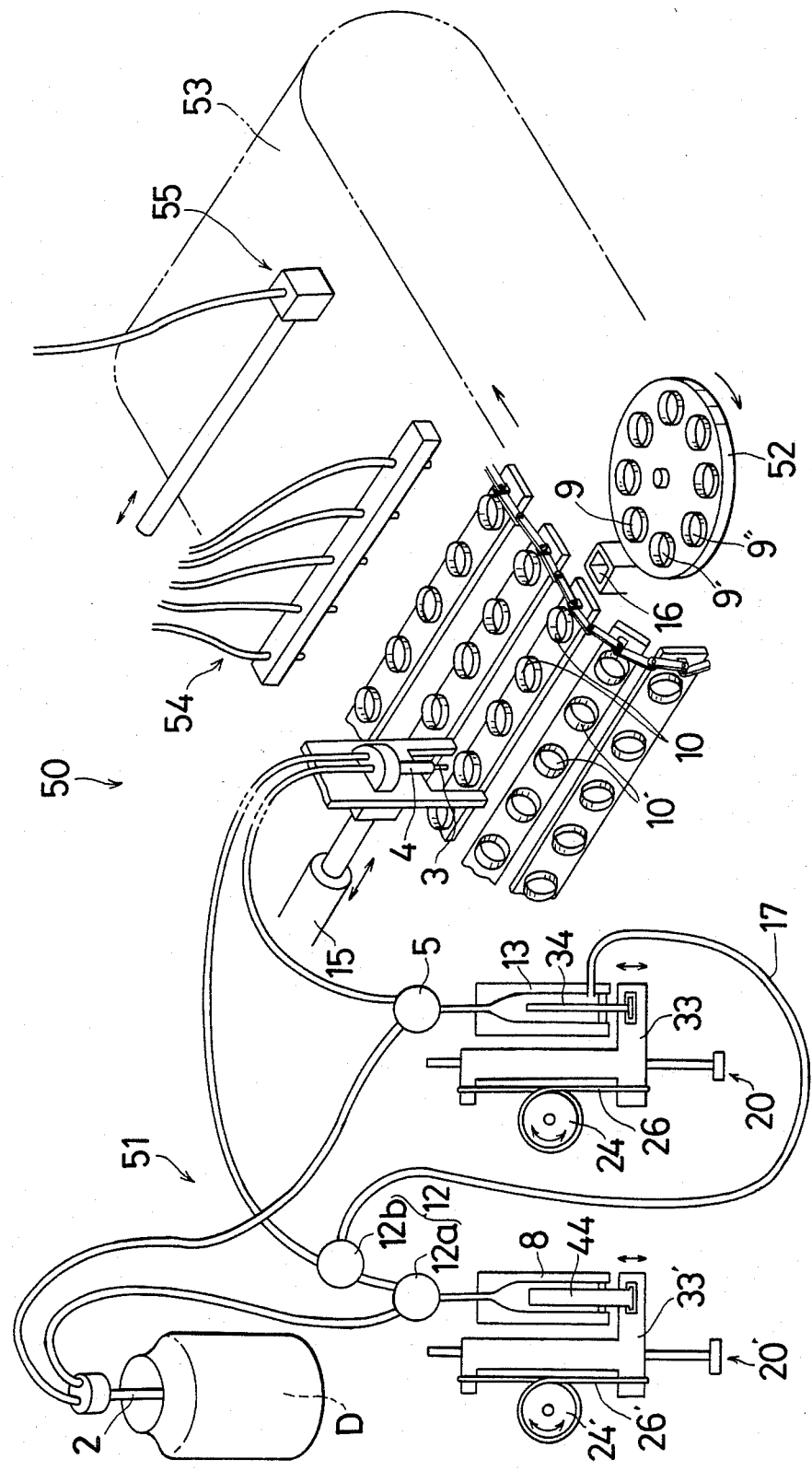
FIG. 8 is a schematic illustration showing one example of an automatic clinical analyzer including a dilution pipetter of the invention.
Figure 9:
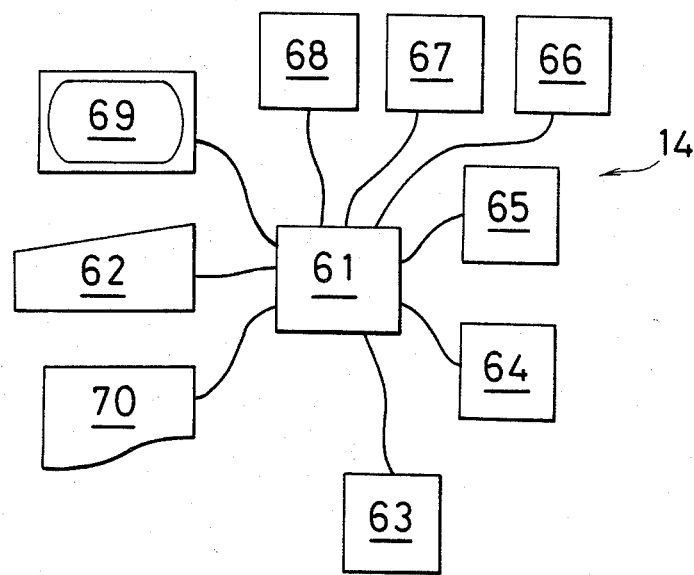
FIG. 9 is a block diagram of a control system employed by the analyzer of FIG. 8.

FIG. 8 and FIG. 9 show a part of an automatic clinical analyzer 50 designed to determine the biochemical components in serum, plasma or urine and including a dilution pipetter 51 as one embodiment of this invention.

The dilution pipetter 51 has substantially the same constitutions as those in the dilution pipetter 11 of the previous embodiment, in which the corresponding components carry the same reference numerals as those for the pipetter 11.

In using the automatic clinical analyzer 50, an operator sets samples to be measured such as serums which have been taken from a plurality of patients into sample cups 9, 9', . . . respectively on a turntable 52 and inputs from a keyboard 62, an identifying code for the sample and the specific items for the analysis to be carried out.

A computer 61 actuates the controller 63 for the moving mechanism 15, the controller 64 for the switching valves 5 and 12 and the controller 65 for the driving mechanisms 20 and 20' to distribute the sample in the sample cup 9 and the diluent D over the reaction tubes 10, 10', . . . Then, a reaction tube moving mechanism 53 is actuated by the relevant controller 66 to move the reaction tubes 10, 10', . . . just beneath a reagent injector 54. At this instance, the reagent injector 54 is actuated by the relevant controller 67 to inject the reagent corresponding to each of the examination items to each of the samples in the reaction tubes 10, 10', . . . After the elapse of a predetermined period of reaction time, the reaction tube moving mechanism 53 is actuated again to move the reaction tubes 10, 10' . . . just beneath a detection probe 55. Then, the detection probe 55 is actuated by the relevant controller 68 to successively suck the liquid from each of the reaction tubes 10, 10' . . . and thereby obtain the result for the analysis by the use of the absorptiometric method. The result thus obtained for the analysis is indicated on a CRT display or outputted to a printer 70.

The same procedures as described above are carried out for the examination on the analytical items inspected with respect to the respective samples charged in the sample cups 9', 9", . . .

Examples for the items of the analysis include alkali phosphatase, amylase, urine esterase, etc.

Figure 10:
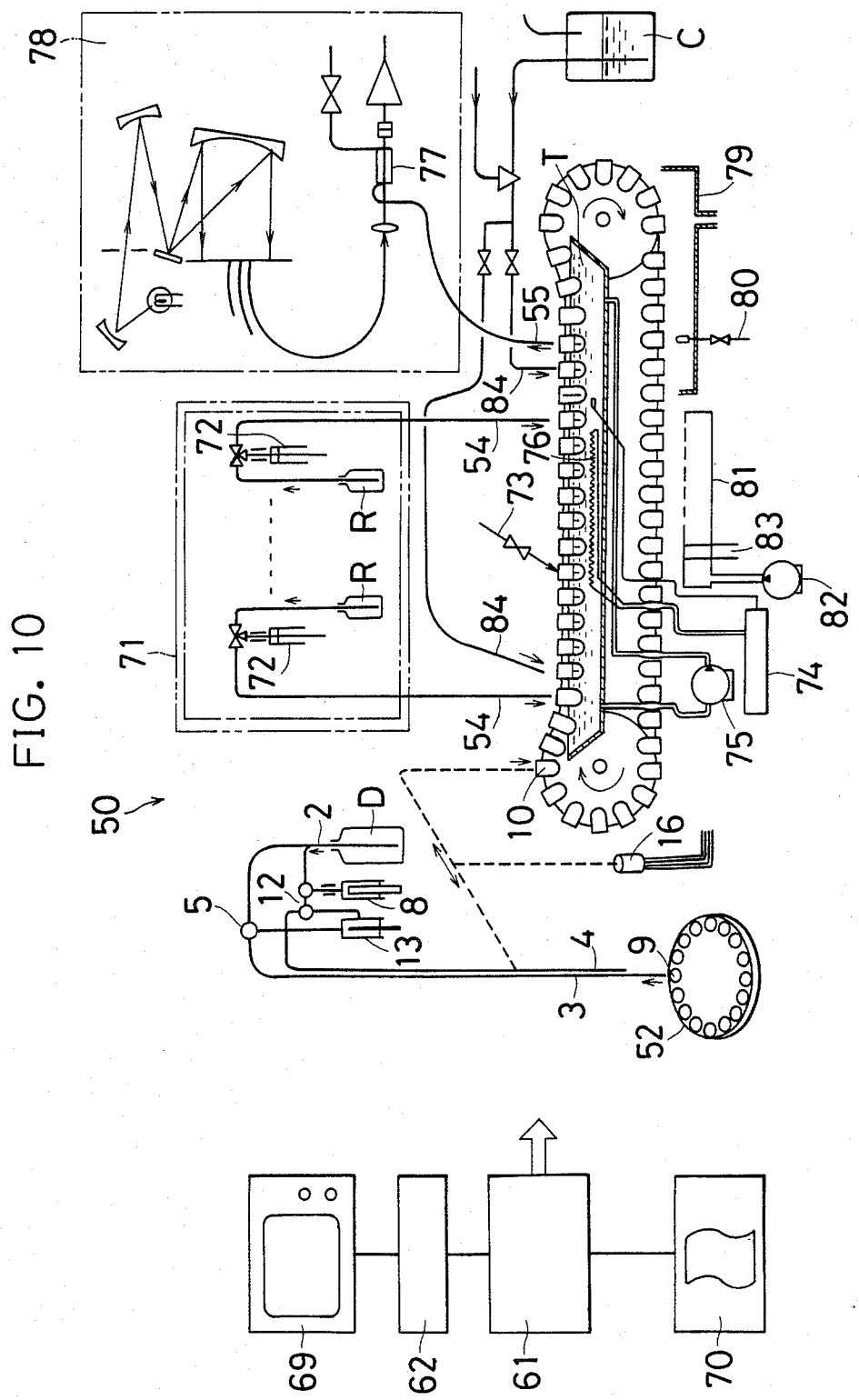
FIG. 10 is a diagrammatic view showing the whole construction of the analyzer of FIG. 8.

FIG. 10 shows a whole construction of the automatic clinical analyzer 50. Elements newly illustrated in FIG. 10 will be explained hereinafter.

Various kinds of reagents R, R', . . . being stocked in a reagent stocker 71 are passed to the reagent injector 54 by means of the dispenser pump 72. Member 84 indicates an injector for providing pure water or detergent C. Member 73 indicates a stirrer. The temperature of each the reaction tubes 10, 10', . . . is controlled in a water bath T keeing a constant temperature, which equips a heater 76, a heater controller 74 and a water pump 75. The liquid after completing the required reaction is sucked by the detection probe 55 and transferred to a flow cell (77) in a photo meter (78) and then analyzed. The remaining liquid in each of the reaction tubes 10, 10' . . . is passed to the waste liquid vessel (79). Then, the reaction tubes 10, 10', . . . emptied are washed by means of a washer nozzle 80 and dried with hot dry air which comes from a duct 81 having a blower 82 and a heater 83.

As many apparently widely different embodiments of this invention may be made without departing from the spirit and scope thereof, it is to be understood that the invention is not limited to the specific embodiments thereof except as defined in the appended claims.

What is claimed is:

1. A dilution pipetter comprising a diluent sucking probe, a sample probe for sucking and discharging a liquid sample, a diluent discharging probe disposed adjacent to the sample probe, a plunger pump of relatively small plunger diameter communicating selectively with said diluent sucking probe or said sample probe by a first switching means, a plunger pump of relatively large plunger diameter, and a second switching means which selectively allows the plunger pump of large diameter to communicate with the diluent sucking probe, the diluent discharging probe, or the sample probe by way of the plunger pump of small diameter.

2. A dilution pipetter as defined in claim 1, wherein the first switching means comprises a 3-way switching valve.

3. A dilution pipetter as defined in claim 1, wherein the plunger pump of small plunger diameter and the plunger pump of large plunger diameter each have a plunger driving mechanism comprising a rotatable cylinder a belt secured to and wound around the surface of the cylinder so as not to overlap, and a slidable moving member secured to both ends of the belt and connected to the plunger of the plunger pump, the belt being wound around the cylinder by the rotational movement thereof, thereby reciprocally linearly driving the plungers of the two plunger pumps.

4. A dilution pipetter as defined in claim 3, wherein the belt comprises a broad wide portion having an elongated hole and a narrow wide portion being capable of being accommodated in the elongated hole the narrow wide portion being wound around the surface of the cylinder while being inserted into the elongated hole in the broad wide portion.

5. A dilution pipetter as defined in 3, wherein the belt is mounted in a stretched state with respect to the moving member of a resilient neans.

6. A dilution pipetter as defined in claim 5, wherein the resilient means comprises a leaf spring mounted at one end of the moving member.

7. A dilution pipetter as defined in claim 1, for use in an automatic clinical chemistry analyzer.

8. A dilution pipetter as defined in claim 1, wherein the plunger of large diameter has a plunger diameter at least greater by the factor of the 2 than the plunger diameter of the small plunger pump.

* * * * *

UNITED STATES PATENT AND TRADEMARK OFFICE
CERTIFICATE OF CORRECTION

PATENT NO. : 4,523,484

DATED : June 18, 1985

INVENTOR(S) : Kadota et al.

It is certified that error appears in the above-identified patent and that said Letters Patent is hereby corrected as shown below:

On the title page, insert a claim for foreign priority to Japanese Patent Application 180916/1982, filed November 30, 1982.

Column 1, line 14, insert --the-- between "as" and "serum", and insert a comma after "animals".

Column 1, line 30, change "to thereby" to --thereby to--.

Column 1, line 39, change "in adjacent with" to --adjacent to--.

Column 1, line 41, change "droplette" to --droplet--

Column 2, line 3, change "restriction of" to --requirement for--.

Column 2, line 40, change "constitutions" to --configurations--.

Column 2, line 68, delete "a".

Column 3, line 24, change "portion 26b being capable to --portion 26b capable--.

UNITED STATES PATENT AND TRADEMARK OFFICE
CERTIFICATE OF CORRECTION

PATENT NO. : 4,523,484

DATED : June 18, 1985

INVENTOR(S) : Kadota et al.

It is certified that error appears in the above-identified patent and that said Letters Patent is hereby corrected as shown below:

Column 4, line 5, change "exerting" to --exerted--.

Column 4, line 61, change "to thereby" to --thereby to--.

Column 5, line 21, change "for" to --of--.

Column 5, lines 24-25, change "in Fig. 2, instead of" to --in Fig. 2 may be--.

Column 5, line 32, change "to desirably" to --desirably to--.

Column 5, line 36, change "including" to --includes--

Column 5, line 40, change "constitutions" to --configuration-- and delete "those in".

Column 5, line 48, delete the comma.

Column 5, line 55, insert a hyphen between "tube" and "moving".

Column 5, line 58, change "instance" to --time--.

UNITED STATES PATENT AND TRADEMARK OFFICE
CERTIFICATE OF CORRECTION

PATENT NO. : 4,523,484

DATED : June 18, 1985

INVENTOR(S) : Kadota et al.

It is certified that error appears in the above-identified patent and that said Letters Patent is hereby corrected as shown below:

Column 5, line 63, insert a hyphen between "tube" and "moving".

Column 6, line 10, change "a" to --the--.

Column 6, line 19, change "keeing" to --holding--.

Signed and Sealed this

Twelfth Day of August 1986

[SEAL]

Attest:

DONALD J. QUIGG

Attesting Officer

Commissioner of Patents and Trademarks